(12) United States Patent
Myllymäki et al.

(10) Patent No.: US 11,317,862 B2
(45) Date of Patent: May 3, 2022

(54) METHOD AND AN APPARATUS FOR DETERMINING TRAINING STATUS

(71) Applicant: Firstbeat Analytics Oy, Jyväskylä (FI)

(72) Inventors: Tero Myllymäki, Jyväskylä (FI);
Joonas Korhonen, Jyväskylä (FI);
Mikko Seppänen, Jyväskylä (FI);
Kaisa Hämäläinen, Jyväskylä (FI);
Veli-Pekka Kurunmäki, Jyväskylä (FI)

(73) Assignee: Firstbeat Analytics Oy

( * ) Notice: Subject to any disclaimer, the term of this patent is extended or adjusted under 35 U.S.C. 154(b) by 182 days.

(21) Appl. No.: 16/862,803

(22) Filed: Apr. 30, 2020

(65) Prior Publication Data
US 2020/0253542 A1   Aug. 13, 2020

Related U.S. Application Data

(63) Continuation of application No. 16/021,450, filed on Jun. 28, 2018, now Pat. No. 10,674,959, which is a
(Continued)

(30) Foreign Application Priority Data

Dec. 21, 2017   (EP) .................................... 17209676

(51) Int. Cl.
*A61B 5/024* (2006.01)
*A61B 5/00* (2006.01)
(Continued)

(52) U.S. Cl.
CPC .......... *A61B 5/486* (2013.01); *A61B 5/02405* (2013.01); *A61B 5/02438* (2013.01);
(Continued)

(58) Field of Classification Search
CPC ........ A61B 2503/10; A61B 2562/0219; A61B 5/02405; A61B 5/02438; A61B 5/1112;
(Continued)

(56) References Cited

U.S. PATENT DOCUMENTS 7,192,401 B2   3/2007   Saalasti et al.
7,330,752 B2   2/2008   Kettunen et al.
(Continued)

FOREIGN PATENT DOCUMENTS

WO   2007/099206 A1   9/2007

OTHER PUBLICATIONS

European Search Report dated May 28, 2018 of corresponding European application No. 17209676.0; 10 pgs.
(Continued)

*Primary Examiner* — George Manuel
(74) *Attorney, Agent, or Firm* — Samuel M. Korte; Max M. Ali

(57) ABSTRACT

A method and system for determining training status of a user from exercises using a device with a heart rate sensor, a processor, memory, an output device and software. The training status is selected from a fixed group of alternatives. Each exercise is monitored using the heart rate sensor. Chosen exercise characteristics of each executed exercise are determined using obtained heart rate data and the determined characteristics of each executed exercise are stored in a memory. The chosen exercise characteristics include values of at least following variables: a date of the exercise, a value depicting physical readiness level for exercise during the exercise, a value depicting a training load of the exercise. When the exercises have been executed, values of selection variables are calculated using the stored exercise characteristics in the memory.

20 Claims, 7 Drawing Sheets

Related U.S. Application Data continuation-in-part of application No. 15/850,642, filed on Dec. 21, 2017, now Pat. No. 10,580,532.

(60) Provisional application No. 62/437,453, filed on Dec. 21, 2016.

(51) Int. Cl.
  *G16H 20/30* (2018.01)
  *G16H 40/63* (2018.01)
  *G16H 40/67* (2018.01)
  *A61B 5/11* (2006.01)

(52) U.S. Cl.
  CPC ............ *A61B 5/4884* (2013.01); *A61B 5/743* (2013.01); *G16H 20/30* (2018.01); *G16H 40/63* (2018.01); *G16H 40/67* (2018.01); *A61B 5/1112* (2013.01); *A61B 5/1118* (2013.01); *A61B 5/1128* (2013.01); *A61B 5/4815* (2013.01); *A61B 5/681* (2013.01); *A61B 5/6898* (2013.01); *A61B 5/741* (2013.01); *A61B 2503/10* (2013.01); *A61B 2562/0219* (2013.01)

(58) Field of Classification Search
  CPC ... A61B 5/1118; A61B 5/1128; A61B 5/4815; A61B 5/486; A61B 5/4884; A61B 5/681; A61B 5/6898; A61B 5/741; A61B 5/743; G16H 20/30; G16H 40/63; G16H 40/67
  See application file for complete search history.

(56) References Cited

U.S. PATENT DOCUMENTS

| | | |
|---|---|---|
| 9,519,755 B2 | 12/2016 | Saalasti et al. |
| 2007/0179357 A1 | 8/2007 | Bardy |
| 2014/0088444 A1 | 3/2014 | Saalasti et al. |
| 2014/0288449 A1 | 9/2014 | Wegerif |
| 2016/0023047 A1 | 1/2016 | Wisbey et al. |
| 2016/0184637 A1 | 6/2016 | Pulkkinen et al. |
| 2016/0220866 A1 | 8/2016 | Feichtinger et al. |
| 2016/0262693 A1* | 9/2016 | Sheon .................. A61B 5/4866 |
| 2016/0324462 A1 | 11/2016 | Hamalainen et al. |

OTHER PUBLICATIONS

Firstbeat Technologies Ltd., "EPOC Based Training Effect Assessment", Mar. 27, 2012, pp. 1-5, Retrieved from the Internet: URL:https://www.firstbeat.com/wp-content/uploads/2015/10/white_paper_training_effect.pdf.

Jill Borresen et al., "Autonomic Control of Heart Rate during and after Exercise", Sports Medi, Adis Press, Auckland, NZ, vol. 38, No. 8, Jan. 1, 2008, pp. 633-646.

"Polar V800 User Manual" with Polar web service, Polar Electro Oy, 133 pgs.

* cited by examiner

METHOD AND AN APPARATUS FOR DETERMINING TRAINING STATUS

CLAIM OF PRIORITY

The present application claims priority from U.S. patent application Ser. No. 16/021,450, filed on Jun. 28, 2018, entitled "Method and an apparatus for determining training status," which in turn claims priority as a continuation-in-part to U.S. patent application Ser. No. 15/850,642, filed on Dec. 21, 2017, entitled "Method and an apparatus for determining training status," which in turn claims priority from U.S. Provisional Patent Application No. 62/437,453, filed on Dec. 21, 2016, the entire contents of which are hereby incorporated by reference.

FIELD

The present method and apparatus relate to determining training status from a group of alternatives during a plurality of exercises and recovery state measurements, where a user has frequently monitored exercises and recovery state measurements with at least heart rate being measured by a host process, which outputs selected variables for calculating the training status by a child process.

BACKGROUND

It is possible for everyone to improve their cardiorespiratory fitness through effective planning of activities. Exercise sessions must be performed frequently enough, and the sessions should regularly include both easier exercise sessions as well as more demanding sessions. In general, sessions should have variation both in their intensity and their duration, and this creates a "training load", a measure of how much the body's homeostasis has been disturbed with training. In addition to changes in daily training load, weekly and seasonal training must include variation. The variation in training load is needed to continue fitness development while avoiding injuries or developing overtraining symptoms.

Monitoring of training load, recovery, and fitness level development is important to ensure that athletes train at an optimal level towards their goal and avoid overloading. Appropriate load and fitness monitoring aids in determining whether an athlete is adapting to a training program and is minimizing the risk of overtraining, developing illness, and/or injury.

To be able to make decisions on future training a user needs to know the current trajectory of their training, referred to as their training status. At certain points in a user's training, they may wish to decrease or increase training in specific ways to elicit a specific reaction, such as peaking for an important race. This requires not only information on each individual exercise, but information on a plurality of exercises to determine the cumulative effect they have had on a user's fitness.

Currently it is not possible to get information on training status based on data from multiple exercises. At first sight that kind of application seems to need a lot of resources. Embedded systems, such as heart rate monitors, fitness devices, mobile phones, PDA devices, tablet computers, or wrist top computers have quite limited CPU and memory resources to be used by any utility application. Those resources are only a fraction of that of an ordinary PC. This is a challenge for an implementation of any physiological method.

Polar V800 with Polar web service (Polar Electric Oy, Finland) presents a system recording training data and giving Training Status from limited group of alternatives. There are physiological conditions which are not identified or that would be very unreliable. Such technically challenging conditions are "Unproductive", "Overreaching", "Productive" or "Peaking".

There are other prior art generally relating to determining a readiness of a user. Document US2016/0023047 (U.S. Pat. No. 9,622,685 B2) presents a system for providing training load schedule for peak performance using earphones with biometric sensors. Document US 2016/0220866 presents a device helping a user to plan the proper timing for setting a next training session.

SUMMARY

The current invention is directed towards a method and apparatus to determine training status from a group of discrete alternatives from a plurality of exercises, where the method can be implemented in an embedded device having limited CPU and memory resources and having a host system. This object is achieved with the features described in accompanying claim 1. The characterized features of the system according to the invention are described in claim 12. In one embodiment the host system uses ETE and THA-libraries, where the ETE is a real-time heart rate analysis library, and THA is a training history analysis library. THA-software is called and executed temporarily to calculate training status value.

In a preferable embodiment the selection of key variables minimizes the demand of resources, particularly RAM memory, and more specifically dynamic memory. The demand of resident memory is very limited, when only characteristics of each exercise are stored. In all embodiments there exists runtime memory with a processor and heart rate data and calculations are stored for a short time in the runtime memory. After each exercise and recovery state measurement their characteristics are stored in the (resident) memory. This data is stored for a longer period. It is used when the training status is calculated.

Training status is determined based on three main parameters: a specific recovery state parameter (or combination of fitness level and recovery state parameter), current short-term training load, and change in short-term training load with respect to previous training. For example, training status calculation analyzes previous training data; current training load, training load changes and variation in fitness level, and a recovery state parameter may be based on heart rate and/or heart rate variability (HRV) indices. Generally speaking there are at least three selection rules with three selection variables, namely one depicting Heart Rate Variability (HRV) and two variables depicting directly or indirectly Short Training Load (ACUTE) and Short/Long Training Load Ratio (TLR).

Training status calculation uses training history data including all kinds of exercise type data. The calculation analyzes absolute training load and saves it to internal memory. If the type of exercise is walking, running or cycling, the user's fitness level may also be analyzed and stored with training load information. Preferably, there is 14 days training history available, and a minimum 7 days. The system will typically store and take into consideration up to 50 days training history.

It can be seen from the literature on physical training that the harder the training has been, the more the homeostasis of the body is disturbed. The more that the homeostasis can be disturbed, the greater the adaptations that can be created in the body and the improvements in physical condition that derive from the adaptations. Thus, measuring disturbance of homeostasis is critical for estimation of training effects in each training session and training load and training effect should reflect the disturbance of homeostasis being induced by each training session. Excess post-exercise oxygen consumption (EPOC) is a measure depicting disturbance of body's homeostasis and therefore suitable for estimating training benefits. Applicant's prior U.S. Pat. Nos. 7,192,401 and 7,805,186 disclose a method for estimating EPOC during exercise and scaling of EPOC values to Training Effect values. Said EPOC estimation method can be applied in this invention in the host process and being combined into calculation of cumulative 7-day loads and respective 7-day target loads in a child process thus forming a part of estimating the short-term and long-term load experienced by the user.

We are using following terms regarding:

Short-term=7 days or less

Long-term=More than 7 days

These are exemplary definitions.

In optimal situations, training status is analyzed with fitness level results. In this situation short-term and long-term training load can be compared to fitness level development. In a preferred embodiment a recovery state parameter or fitness level parameter and the recovery state parameter can be used in combination to determine training status. Both the fitness level parameter (VO2max) and recovery state—parameter depict user's ability to execute training. For example, if fitness increases and/or recovery state parameter are at a good level, an individual is responding well to training and can safely continue training as before. Vice versa, if fitness decreases or recovery state levels are poor they are an indication of poor training response and at least some elements of training should be changed. In one embodiment recovery state parameter is measured in standardized conditions meaning e.g. a short resting measurement while awake or a sleeping measurement. Fitness level and recovery state changes give physiological information which help to identify more challenging training status alternatives.

The invention relates to method for determining a training status of a user from a plurality of physical exercises and recovery state measurements using a portable device with a heart rate sensor, the device having a processor, a memory containing runtime and resident memory, and software, the determined training status being selected from a fixed group of alternatives depicting a unique physical condition of the user.

According to the invention method has steps of measuring heart rate data during each exercise using the heart rate sensor and storing heart rate data into a runtime memory, measuring heart rate data frequently during recovery state measurements using the heart rate sensor and storing heart rate data into a runtime memory determining chosen characteristics of each executed physical exercise, determining chosen characteristics of each recovery state measurement, and storing into a resident memory the determined characteristics of each executed exercise and determined recovery state, respectively, after each exercise/recovery state measurement:

the chosen characteristics including values of at least the following variables:

for each physical exercise:
a date stamp of physical exercise,
; and
a value depicting training load of exercise, and for each recovery state measurement, respectively:
a date stamp of each recovery state measurement,
a value depicting instantaneous person's recovery state; and and method comprising further steps of calculating values of selection variables using the stored characteristics in the resident memory, when the plurality of exercises and recovery state measurements have been executed, and storing calculated values into runtime memory and determining the training status using sequential pre-determined selection rules, each rule being connected to one unique variable of said selection variables, wherein each selection rule uses a calculated value of its selection variable to limit a number of remaining alternatives and, after all selection rules have been sequentially used, only one alternative is selected.

The first and second selection variables describe short and long-term training loads. The same information may be presented in many ways. In this context there are used the terms: short-term training load, herein "ACUTE" and the ratio of the short and long training loads, herein "TLR". The first selection variable may present said TLR and the second variable said ACUTE. The third variable may present a measured recovery status.

The parameter "physical readiness" may refer to a user's fitness level (VO2max), but as FIG. 1B shows it may also refer to measured recovery status depicted by, for example, heart rate variability (HRV, FIG. 1B), and it describes how a user has recovered from physical exercise(s) and how capable their body is to perform coming exercise(s).

The first selection may select a group from a set of groups covering all said training status alternatives and the second selection may select the training status alternative or a pair of alternatives from the first selected group.

It may be understood that the first, second and third variables may be in a different order. However, the chosen selection of variables is an important factor to achieve accurate results with a minimal use of CPU/memory resources.

Of course, it would also be possible to implement said three selection rules as a 3-dimensional look-up table, where the result is picked by a vector having values of said three parameters, which may require more CPU/memory use.

In one embodiment the characteristics of exercises are calculated by a host process having a specific library software (ETE) and a resident memory to store the characteristics for later use. Then a software forming a child process to calculate an actual training status is provided by separate library software (THA), where the child process uses a minimum amount of dynamic, e.g. runtime memory, and the calculated training status vanishing after it has been returned as a result to the host process.

According to another embodiment there is a third variable to be classified and obtaining a third selection for selecting the training status from said pair of alternatives, and wherein the third variable may be a training load trend.

Short-term training load (ACUTE) may be determined according to training history based activity class and absolute weekly training load (a sum of a plurality of days). In another embodiment there can be two additional statuses:

"Recovery" and "Peaking" in use-cases where longer exercise history can be inputted to calculation.

Recovery state can be measured with an analysis of HRV. As HRV values are very individual, the recovery state values can be personally scaled by taking into account the typical values and range of HRV for each person. Scaling of personal training load and recovery state can be calculated by the THA library. The "personalization" requires additional data from background data.

The method could be implemented in any device comprising a processor, memory and software stored therein and a user interface, for example, a heart rate monitor, fitness device, mobile phone, PDA device, wrist top computer, and the like. The implementation may use a minimum amount of RAM memory and CPU-time.

BRIEF DESCRIPTION OF THE FIGURES

Advantages of embodiments of the present disclosure will be apparent from the following detailed description of the exemplary embodiments. The following detailed description should be considered in conjunction with the accompanying figures in which the figures may show exemplary embodiments of the method and apparatus for determining training status from a group of alternatives during exercise season. Figures are only exemplary and they cannot be regarded as limiting the scope of invention.

Figure 1A:
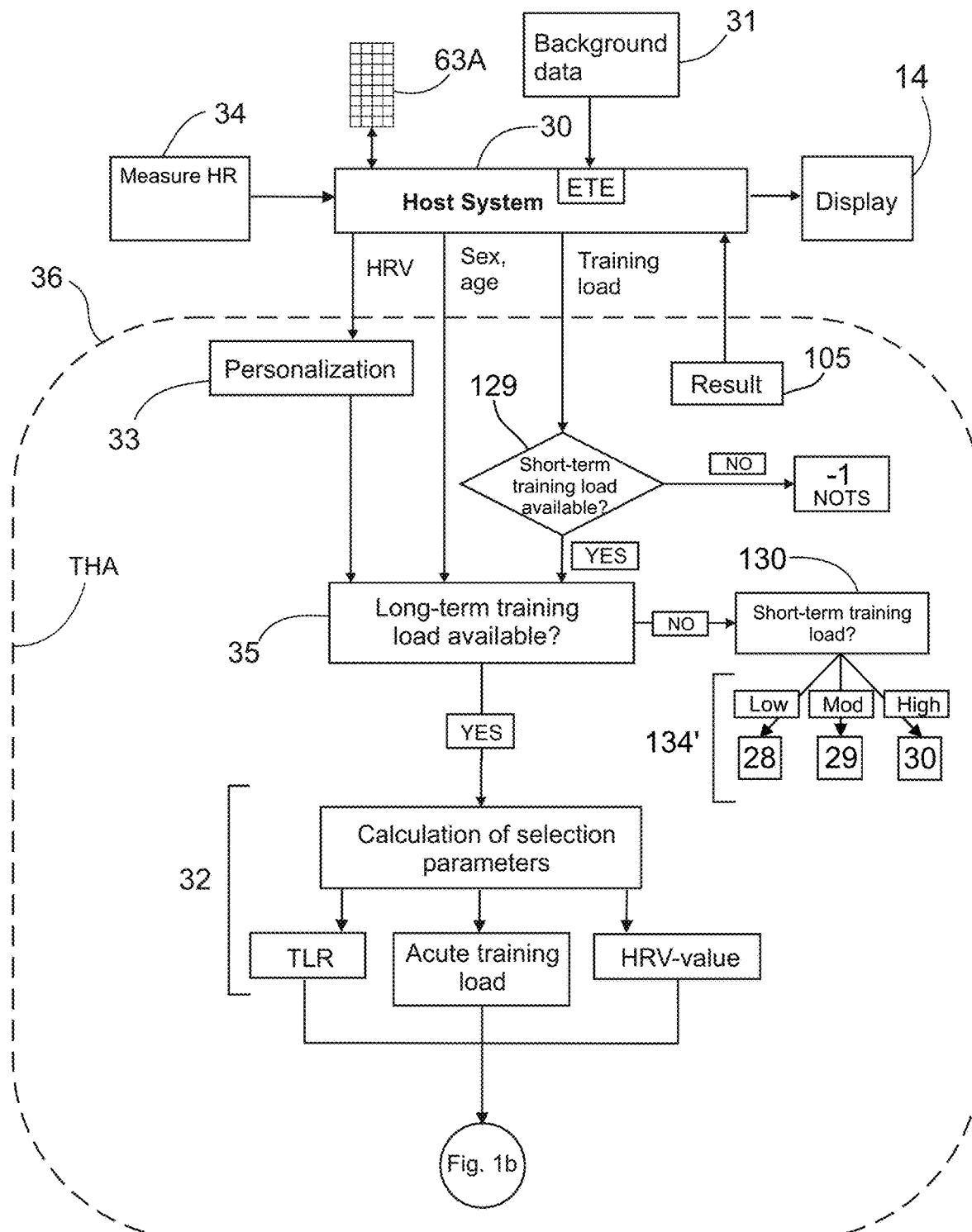
FIG. 1A represents the training status calculation steps of a child process and its connection to a host system

| Term or abbreviation | Definition |
| --- | --- |
| HR | Heart rate (beats/min) |
| HRmax | Maximum heart rate (of a person) (beats/min) |
| VO2 | Oxygen consumption (ml/kg/min) |
| Physical Readiness | Fitness level or recovery state parameter depicting user's ability to exercise |
| VO2max | Fitness level, maximum oxygen consumption capacity of a person (ml/kg/min) |
| Training Load | A measure of the amount of training a person has performed, and may take various forms. One can measure training load in a single session, or cumulatively over a period of time. More or harder training will have a higher training load. There are short (ACUTE) and long-term training load. |
| TLR | The ratio between long-term and short-term training load |
| HRV | Heart rate variability meaning the variation in time interval between successive heart beats. The magnitude of heart rate variability may be calculated from electrocardiographic or photoplethysmographic signals, for example. |
| EPOC | Excess post-exercise oxygen consumption. As it can be nowadays estimated or predicted - based on heart rate or other intensity derivable parameter - it can be used as an cumulative measure of training load in athletic training and physical activity. |
| TRIMP | Training Impulse score. A cumulative measure of the impact of a training session |
| Recovery state parameter | A parameter depicting how well person or athlete has recovered from prior training. A recovery state parameter may be based on measured heart rate and/or heart rate variability (HRV). Recovery state can be evaluated also using, for example, sleep quality, as overtraining may provoke sleep disturbance. |

DETAILED DESCRIPTION

Aspects of the invention are disclosed in the following description and related drawings directed to specific embodiments of the invention. Alternate embodiments may be used without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", embodiments" or "invention" do not require that all embodiments of the invention include the discussed feature, advantage or mode of operation.

When at least 7 days of training history data is available training status can be determined using the following steps, as shown in FIG. 1, and will be described in further detail below.

1. Heart rate variability values are calculated in a host system from each recovery state measurement (e.g. from ECG, or PPG signals)
2. Absolute training load (EPOC and/or TRIMP) is calculated in a host system from each exercise heart rate
3. Transferring HRV, absolute training load and background data to a child system as an input
4. Personalized scaling of HRV data
5. Short-term training load is calculated
6. Long-term training load is calculated
7. Heart rate variability-value is calculated from scaled HRV data
8. Processing the training load ratio, short-term training load, and HRV data and determine training status as shown in FIG. 1B.

Figure 1B:
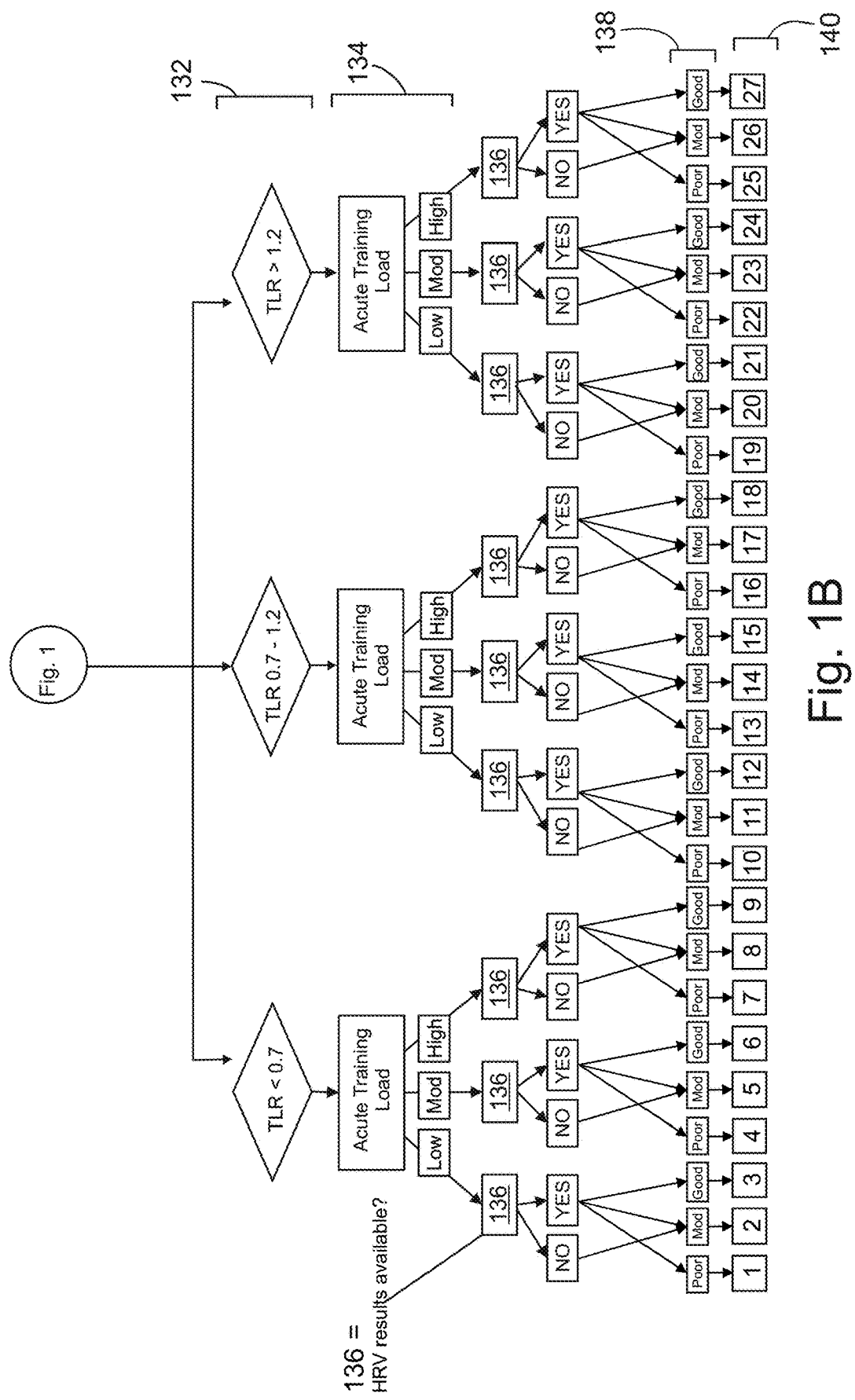
FIG. 1B represents an exemplary embodiment for calculation of training status

Referring to FIG. 1A, a host system 30 and a child system 36 is shown. The host system receives background data, which may include demographic information of the user like gender, age, height, weight, personal HRV range, physiological data like resting or maximum heart rate, or other well-known variables. The host system also receives measured heart rate (heartrate sensor 34), external workload data, and may also receive other context data such as information on previous exercise sessions or exercise type information. The host system 30 stores characteristics and separate recovery state results in a resident memory 63A, which data is called by the child system 36.

The training load is a peak value regarding training effect measured as a disturbance level of homeostasis. Alternatively, a TRIMP score may be used as a measure of training load.

Exercise heart rate may be received from any type of available heart rate data collection apparatus, such as devices collecting electrocardiogram (ECG) or photoplethysmogram (PPG) data. In an exemplary embodiment, these collection apparatuses include portable devices such as a wrist top device with a heart-rate transmitter, a mobile device such as a phone, tablet or the like, or other system having CPU, memory and software therein.

External workload may be derived from any suitable form of device that can collect external workload, depending on the activity in question, and may include global positioning satellite data, accelerometers, measured power output, positioning detection using Wi-Fi, motion capture cameras, or other detection devices of a similar nature known to a person of average skill in the art.

Within the host system 30, measured heart rate is used to determine a heart rate variability measure and training load peak. Training load is defined using existing physiological values that represent the impact a particular exercise session has on the body, often influenced by the intensity and the duration of the exercise session. In an exemplary embodiment, the physiological values of Excess Post-Exercise Oxygen Consumption (EPOC) and Training Impulse (TRIMP) are used, though other known values that serve a similar purpose may also be used. By measuring training load peak of values like EPOC or TRIMP, a singular absolute training load value for each exercise session is calculated and stored. If there are multiple training sessions being held in one day, the absolute training load value for a particular day may also be calculated as a sum of each session's training load peak value.

The host system 30 transfers the calculated heart rate variability measure and absolute training load and background parameters (e.g. age, gender, height and weight) from the resident memory 63A to the child system 36 as an input, which stores all data to the runtime memory.

The heart rate variability and absolute training load are loaded into calculation module 32 of child system 36, which calculates values that will be used in the selection functions including a long-term to short-term training load ratio (TLR), short-term training load (ACUTE) and a heart rate variability-value (HRV), There are certain actions and tests for input parameter before selection parameters can be calculated. The values of HRV are adapted by the step 33 according to personal data (typical HRV-range). Training load values are checked in the step 129 and if there are not enough short-term values, no result is given. If it is checked in the step 35 that there is not long-term training load values available, the user still gets a limited result in the steps 130 and 134' (HRV-values).

The child system 36 enters the chosen training status value result 105 back to the Host system 30, which may show it on the display 14. Optional additional information may also be submitted to the Host System 30 (not shown), for example a selection of additional information according to at least one additional variable depicting at least one of: number of HRV-data, fitness level (VO2max), anaerobic training effect, training variability or high intensity training count.

When all three parameters are valid the calculation module 32 calculates selection parameters a long-term to short-term training load ratio (TLR), short-term training load (ACUTE) and a heart rate variability-value (HRV). These parameters are then forwarded to the selection rules shown in FIG. 1B.

In an exemplary embodiment, shown in FIG. 1B, a heart rate variability (HRV) based recovery test may be used to determine a training status. "Recovery test", for example "Quick recovery test (QRT)" is also herein referred to as an exercise. User starts and stops intentionally that 'exercise' as any other exercise. There are two options for how to handle HRV recovery tests in this "HRV" embodiment.

1. Use a 7-day window, and in optimal case use average result of the HRV measured during relaxation exercises from the last three measurements.
2. Use a 14-day window and take a weighted average of the HRV results from the last three measurements, in which the weighting is based on timing of the relaxation exercises relative to the point when the status is determined. The recent history gets higher weight than more distant history.

Option 1 is described below.

Table 1 illustrates a calculation flow. A female user has monitored her exercises during one month. The host process with ETE-software determines the characteristics of each exercise (training load peak, exercise type) after they are performed, and stores it in a resident memory. In this instance, the term "peak" is calculated peak value of training load during an exercise, and "Type" refers to the type of exercise (0=run, 1=cycling, empty=not known). The HRV column presents single quick recovery test values. In the HRVavg column there is calculated an average value from the last 3 quick recovery tests and HRV classification is determined based on these average-values. HRV classification is coded as 0=not available, 1=poor, 2=mod, 3=good. This half of the table grows row by row and is continuously available. Number coding for WTL trend-values: 0=decreasing, 1=stable, 2=Increasing.

TABLE 1

| date | HRV | HRVavg | HRV classification | Peak | Age | Sex | Type | WTL | WTL Trend | STATUS |
|---|---|---|---|---|---|---|---|---|---|---|
| 9 Jun. 2017 | — | — | 0 | 48 | 29 | 1 | 1 | 1 | 2 | NO_RESULT |
| ... | | | | | | | | | | |
| 14 Jun. 2017 | 20 | — | 0 | 94.1 | 29 | 1 | 1 | 3 | 2 | NO_RESULT |
| 14 Jun. 2017 | | — | 0 | 80.9 | 29 | 1 | 0 | 3 | 2 | NO_RESULT |
| 15 Jun. 2017 | 25 | — | 0 | 93.5 | 29 | 1 | 0 | 3 | 2 | PRODUCTIVE |
| 16 Jun. 2017 | 30 | 25 | 1 | 111.0 | 29 | 1 | 0 | 3 | 2 | UNPRODUCTIVE |
| 17 Jun. 2017 | 55 | 36 | 2 | 127.9 | 29 | 1 | 0 | 3 | 2 | PRODUCTIVE |
| 18 Jun. 2017 | | | | 104.4 | 29 | 1 | 0 | 3 | 2 | PRODUCTIVE |
| 18 Jun. 2017 | | | | 30.5 | 29 | 1 | 0 | 3 | 2 | PRODUCTIVE |

TABLE 1-continued

| date | HRV | HRVavg | HRV classification | Peak | Age | Sex | Type | WTL | WTL Trend | STATUS |
|---|---|---|---|---|---|---|---|---|---|---|
| 19 Jun. 2017 | | | | 108.1 | 29 | 1 | 0 | 3 | 2 | PRODUCTIVE |
| 19 Jun. 2017 | 75 | 53 | 2 | 83.4 | 29 | 1 | 1 | 4 | 3 | PRODUCTIVE |
| 20 Jun. 2017 | 80 | 70 | 3 | 90.3 | 29 | 1 | 1 | 4 | 3 | PRODUCTIVE |

The right section of the table is temporal data. The selection parameters Weekly Training Load (WTL) and WTL trend are calculated only when desired. The software from THA-library is first called and loaded. The training status "STATUS" is returned to the host process, which presents it in a display. After the result has been outputted to the host process, the child process and its temporal data in one row vanish.

Considering the HRV embodiment, arithmetic HRV average or weighted HRV average (e.g. from quick recovery tests) describes a state for a given day in such a way that calculation of trend may not be required.

In recovery tests here, the results may be scaled to 0-100 scale based on individuals typical HRV levels and their typical deviation (range). 0-100 scaling can be used regardless of absolute HRV values or algorithms used for analyzing recovery from relaxation exercises. A recovery test describes how well an athlete is recovered from previous training sessions and may produce a numerical score or a text result representing the athlete is within a particular zone, such as "poor recovery", "moderate recovery" (mod) or "good recovery". It should be obvious to someone skilled in art that the system could also work in a way that recovery state value is used in combination with fitness level value: I.e. Instead of recovery state only a readiness index would be calculated that would reflect both recovery state and fitness level (VO2max) trend.

Referring still to FIG. 1B, the short-term to long-term training load ratio (TLR) of step 132, compares recent training load to the training load over a longer period of time, which may determine whether the intensity of the most recent bouts of training are increasing relative to previous time periods. The ratios of step 132 serve as example upper and lower limits and said limits may be adjusted as appropriate to reflect the demands of a particular sport. In step 134, the acute training load, which may be the training of the last 7 days, is determined. The training load measurement may take the form of "low", "moderate", and "high" as shown in FIG. 1B, In step 136 of FIG. 1B, the system will determine whether sufficient recovery state (HRV) data is available. A normal expectation is that at least 3 recovery tests done in a week to provide the most accurate measurement of a person's recovery over the previous week of training. However, the system may still provide a training status assessment even when the number of HRV recovery tests is too low. As shown in step 138, the different levels of recovery test scores will result in different training feedback sentences. The training statuses are determined in step 140. For clarity, only the numerical training feedback sentences are shown in FIG. 1B. The step 140 use statuses which correspond to the alternatives shown in Table 2. As disclosed above, training status may be available even without HRV results as shown in step 130 when there is only short-term training load available, and step 136 where short-term and long-term training load is used and the missing HRV result is considered equal to "moderate" HRV result. In step 129, lacking short-term training load information leads to unavailable training status feedback (NOTS=No Training Status).

Example Feedback Sentences and Statuses Related to Exemplary Recovery State (HRV) Embodiment Presented in Step 140 Of FIG. 1B—Table 2

Feedback Training

| Number | Status | Long Feedback sentence |
|---|---|---|
| −1 | Not available | Training Status not available due to lacking exercise history. |
| 1 | Fatigued | Unfresh, poorly recovered although unloading. |
| 2 | Recovery | Ready to increase training. |
| 3 | Peaking | Very good readiness to increase training or perform at best. |
| 4 | Overreaching | Overreaching after rather demanding training period. Poor recovery. |
| 5 | Recovery | Taking easier after demanding training period. |
| 6 | Peaking | Taking easier after hard period, your body seems to have good readiness to perform at best. |
| 7 | Fatigued | Overreaching, fatigued state. Pay attention on recovery! |
| 8 | Overreaching | Overreaching state. |
| 9 | Productive | Training hard although the load is decreasing, the body is responding well to training. |
| 10 | Fatigued | Easy period behind, but body is not responding well. |
| 11 | Detraining | Balanced but easy training. |
| 12 | Maintaining | Balanced but easy training. The body would be ready for increased training load. |
| 13 | Unproductive | Training in balance, but recovery challenges. |
| 14 | Productive | Good work, productive training. |
| 15 | Productive | Excellent training state, everything in balance. |
| 16 | Overreaching | Overreaching after long period of hard training. Pay attention on recovery. |
| 17 | Productive | Continuously hard training, pay attention on recovery. |
| 18 | Productive | Continuously hard training, body responding well. |
| 19 | Fatigued | Started to increase training after detraining period, body responding poorly. Pay attention on recovery! |
| 20 | Productive | Started to increase training after detraining period. |
| 21 | Productive | Started to increase training after detraining period, body responding well. |
| 22 | Fatigued | Increased training load to moderate levels, body responding poorly. |
| 23 | Maintaining | Increased training load to moderate level. |
| 24 | Productive | Increasing training load, body responding well. |
| 25 | Fatigued | High training load is poorly tolerated. Focus on recovery! |
| 26 | Overreaching | Training load has increased to high level, pay attention on recovery. |
| 27 | Productive | Training load has been increased to high level, but the body responding well. |
| 28 | Maintaining | Training easily. |
| 29 | Productive | Training moderately. |
| 30 | Productive | Training hard. |

Option 2

In the second option of this embodiment, calculation of the recovery state can be performed using a 14-day window using a weighted average of the previous three HRV test measurements. The results are weighted based on the timing of the recovery tests, a weighted least squares fit is used so that newer results get higher weight than older tests (and therefore emphasized more than older days in the training history).

Optionally, the method may also take into account the number of consecutive rest days an athlete has taken. If a certain number of rest days have been taken consecutively, regardless of the short-term or long-term training load, a "detraining" training status may be triggered. Additionally, a threshold for the detection of consecutive rest days may be adjusted based on the person's identified activity class. Exercisers who may have a lower activity class might, for example, receive a detraining warning after 5 consecutive rest days, while an elite athlete with a high activity class may receive that warning after only 2.

Personal Scaling of Training Load

The step of personalization 33 may be used in scaling the training load measures based on personal training history. Regarding short-term training load, a personal scaling can be performed for example by calculating:

1. Short-term training load being the TRIMP sum during the last 7 days
2. Defining the personal upper limit (maximal) load based on training history being the highest short-term load found from the training history being up to one year of data
    a. If acute load gets higher than the last maximum acute load value, increase it to the closest 100-round figure that is above the acute load.
    b. The upper limit may be decreased by for example 100 when
        i. Acute load has been lower than maximal load minus 100 for the last two weeks and there is over a 14 days of training history data
    c. Maximal acute load limit value may be limited to a predetermined value, for example over 500 units of TRIMP. That value could be used even though there were no training sessions in the history Regarding long-term training load, it may be calculated as:

1. Average acute load of the last 4 weeks.
2. It may be determined also for histories with only 7 days of training history by extrapolating the 7-day value to represent a typical week for the individual.
3. May not be determined if there are less than certain amount of exercise sessions, for example 3, during the last 4 weeks.

Figure 2:
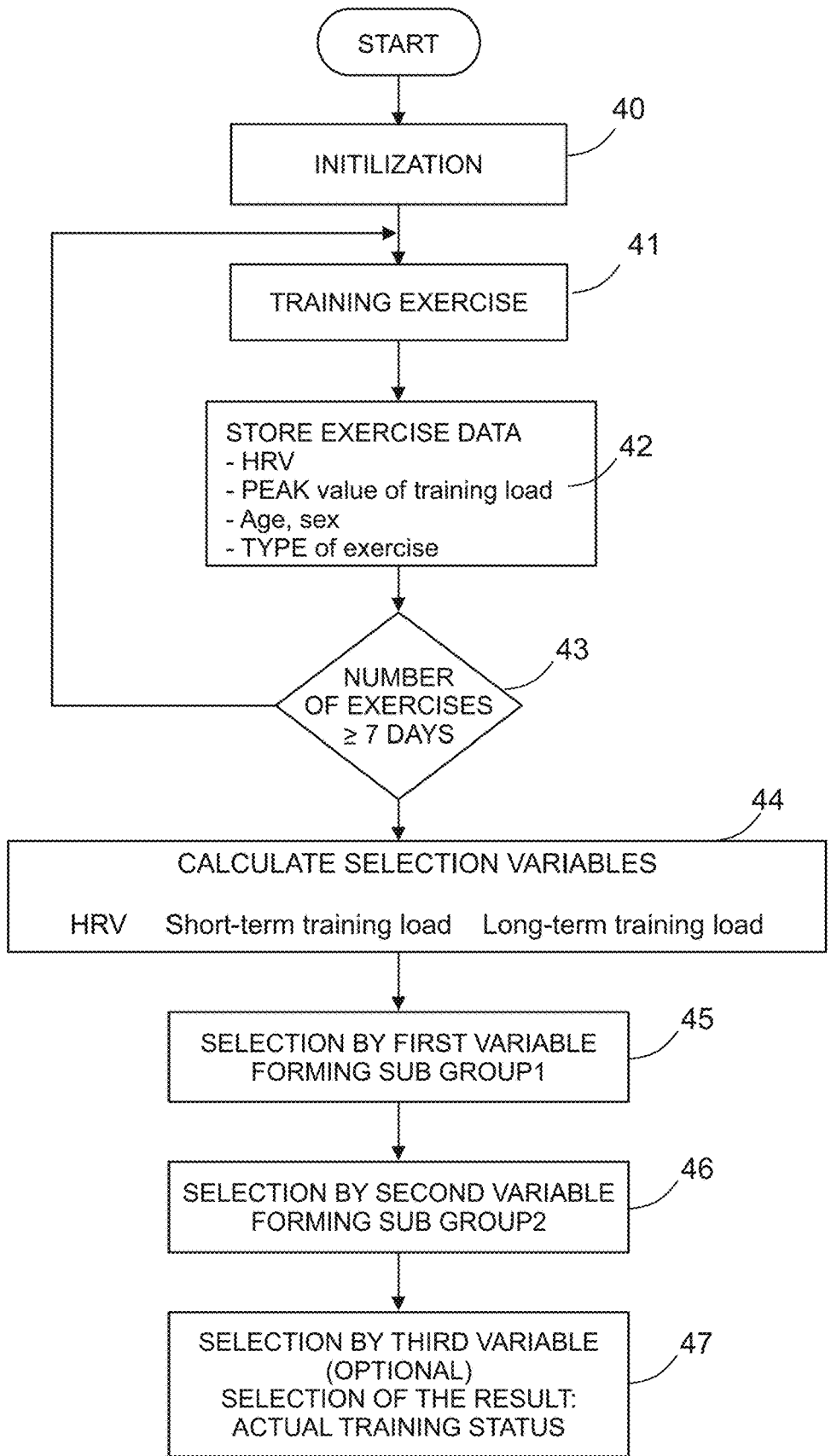
FIG. 2 presents a flowchart visualizing the process of determining the training status

The different components are given a reliability score as follows:

1. Short- to long-term training load score reliability
    Weight=0.0→poor
    Weight=0.5→moderate
    Weight=1.0→good
2. Quick Recovery Test score reliability
    Weight >=0.0→poor
    Weight >=0.15→moderate
    Weight >=1.0→good The Flowchart of the Execution of Software (FIG. 2)

The host process is continuously running by a host system 30. After, a start software initializes (step 40) the child process and populates background data in runtime registers. When an exercise starts the host process calls specific software from the library ETE, which takes care of ordinary calculation and monitoring of exercises and calculates desired physiological results, including characteristics of each exercise. Each exercise is monitored in step 41 and after that the characteristics, i.e. the values of specific parameters are stored to a resident memory in step 42. Those specific parameters are date, training load peak for each exercise and optionally exercise type for each date, HRV results for each day (referring to recovery state), age and sex from which other parameters can be derived (TLR (ratio), ACUTE (short-term training load), HRVavg). In a step 43 there is a check whether there are enough data for calculation of training status. If number of exercises is too low, the execution returns to monitor next exercise, otherwise the child process is called from library THA. The characteristics are fed to runtime registers and the selection variables are calculated in step 44.

A triphasic selection (steps 45, 46, 47) leads into determination of the final result (step 105 in FIG. 1A): the step 45 selects subgroups I using the value of the training load ratio. A few results can be picked up directly in certain combinations in next step 46 using the value of the weekly training load, but otherwise there are subgroups II each having two or more alternatives. The result will be obtained always at least using third selection in step 47 using the recovery state value.

Absolute and Relative Training Load and Training Load Trend Calculation

Absolute training load is a calculation of the total training load over a selected period of time and may utilize a cumulative physiological score based on EPOC and TRIMP scores. Training load may be calculated according to U.S. Pat. No. 7,192,401 (B2) "Method for monitoring accumulated body fatigue for determining recovery during exercise or activity", incorporated herein.

The step 134 of the training status calculation shown in FIG. 1B utilizes acute training load calculations provided by the calculation module 32. Relative weekly training load may be determined based on user's activity class where activity class may be based on a user's background information, such as age or gender, or a VO2max value and long-term training load. Relative training load may be represented by, for example, 6 levels (0-5). Relative training load is 0 if absolute weekly training load is 0. If absolute training load is more than 0 relative training load may be determined according to FIG. 3. Of course, a less granular way can be used as well, such as utilising a scale with terms like "low", "moderate", and "high" as in FIG. 1*b*

Figure 3:
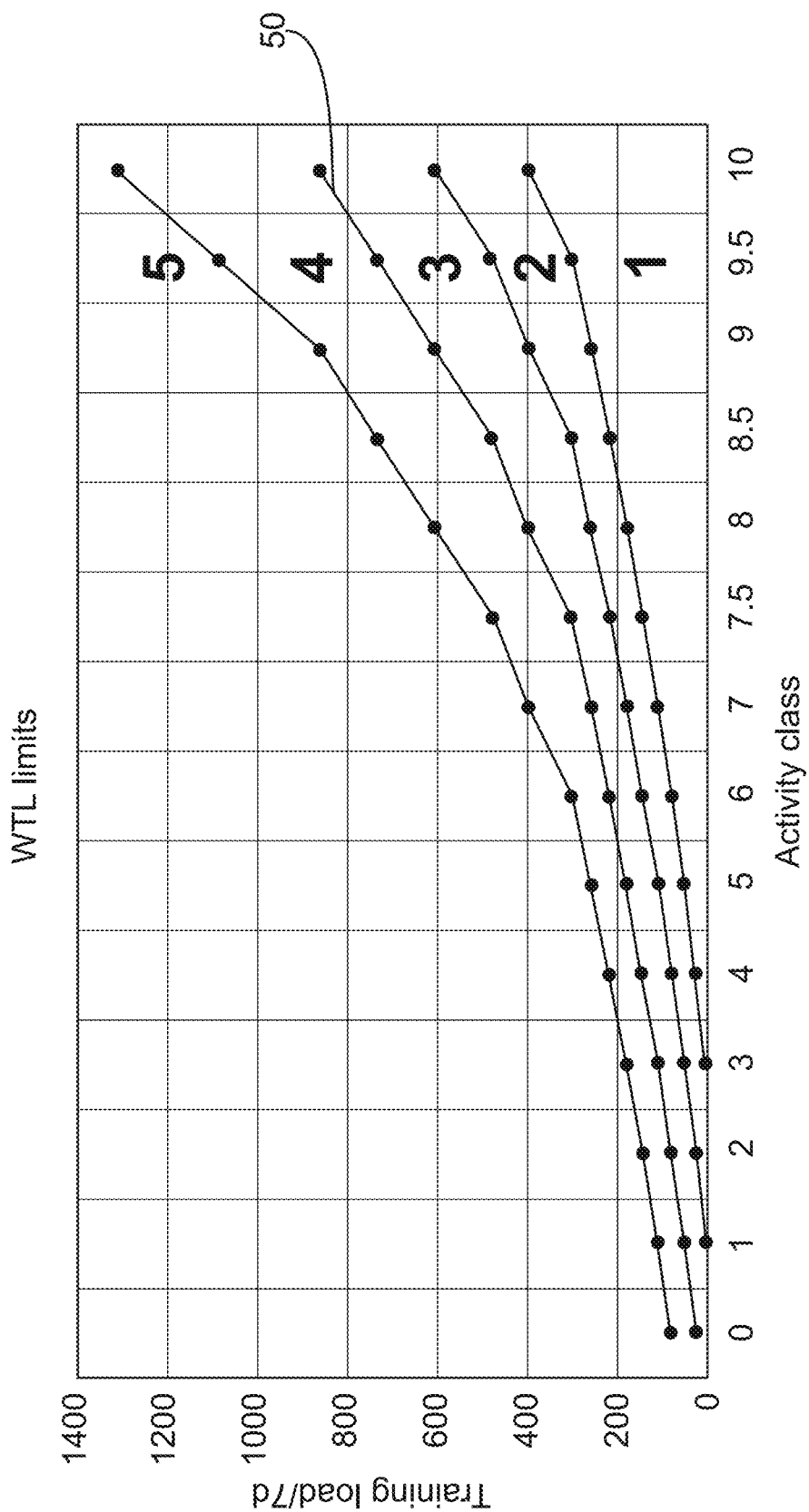
FIG. 3 represents relative weekly training load lower limits (0-5)

Referring now to FIG. 3, activity class is a general descriptor of a person's fitness or training history, placed on a 0-10 scale, wherein 0 represents a person who is essentially entirely sedentary, and 10 is a highly trained individual who exercises regularly. Each plot line of FIG. 3 represents the lower limit of the cumulative training load to reach a given relative training load level. By way of example, plot line 50 represents the line wherein a person that exceeds a particular training load will be given a relatively weekly training load value of 4. An athlete with an activity class of "8" that exceeds an absolute training load over a 7-day period of 400 may therefore be given a relative training load value of 4. However, a different person with an activity class of "9" with a similar absolute training load may only receive a relative training load value of 3. For example, reaching an average relative training load value of 3.5 (e.g. over a 4 week period) can be used as a limit value for updating activity class upwards and 3.0 as a limit to maintain current activity class.

In one exemplary embodiment, in the case where no new exercise data has been input, the system will still be able to provide training status. The training statuses of "0—Detraining", "4—Recovery", and "no status" statuses can be outputted without new exercise data. Other states require at least a new training session to update the training status.

In an alternative embodiment, other physiological signals other than heart rate may be used to measure training load. For example, electromyography (EMG) signals could be used to measure muscular training load. End users may be able to utilize the various apparel that is available on the market that measures EMG-signals to measure muscular training load data and can provide data for the system.

In still another alternative embodiment, with respect to FIGS. 1A, 1B and 2, sleep quality and/or stress levels measured during daily life or other separate measurements may be taken into account in training status determination. Calculation of such metrics may take place in host system 30 and calculation of said metric is disclosed e.g. in U.S. Pat. No. 7,330,752 (B2) "Procedure for Detection of Stress by Segmentation and Analyzing a Heart Beat Signal", U.S. Pat. No. 9,519,755 (B2) Method and System for Evaluating a Physiological State Depicting a Person's Resources" and/or US patent application 2016324462 (A1) "Method and System for Providing Feedback Automatically on Physiological Measurements to a User". For example, if training load is high, results from a night time measurement or separate recovery tests could be used as additional information in training status determination. Of course, recovery state could be estimated by measuring for example heart rate and HRV during nightly sleep which may in some cases enable better reproducibility of results when compared to a quick test. In order to achieve even more standardized conditions, the previous embodiment could be tuned in a way that the exemplary HRV index would be calculated during a specific sleep stage, such as deep (slow wave sleep). If sleep stage detection is not possible, sleep recovery state can be calculated also from a predetermined time period during the night, such as a 4-hour period starting from sleep onset. Another possible embodiment is the use of sleep quality in estimating training status. For example, low sleep quality can be used as an additional parameter increasing the likelihood of overreaching or overtraining as both conditions are known to provoke sleep disturbance.

Training status is presented to a user in a variety of different ways; exemplary embodiments are shown in Table 2 and FIGS. 4-7. The presentations of training status may be adapted as appropriate to the device's display that is being used. Table 2 shows a number of text alternatives for describing training status, including a longer description of each status, a text representation of the relative weekly training load value and recovery state, a sample explanation of the training that may lead to selection of that particular training status, and a sample piece of text that may be presented to a user providing guidance about future training. Training status could be updated daily or weekly. If training status is updated on a weekly basis (instead of daily basis) one possible method for analyzing weekly status is to show the mode of the daily status during the week. If two or more different statuses appear equally frequently during last 7 days then weekly status is chosen according to pre-set priority rules, which may include a specific activity chosen by the user, and averaging of the most common activity over a specific period of time.

Figure 4:
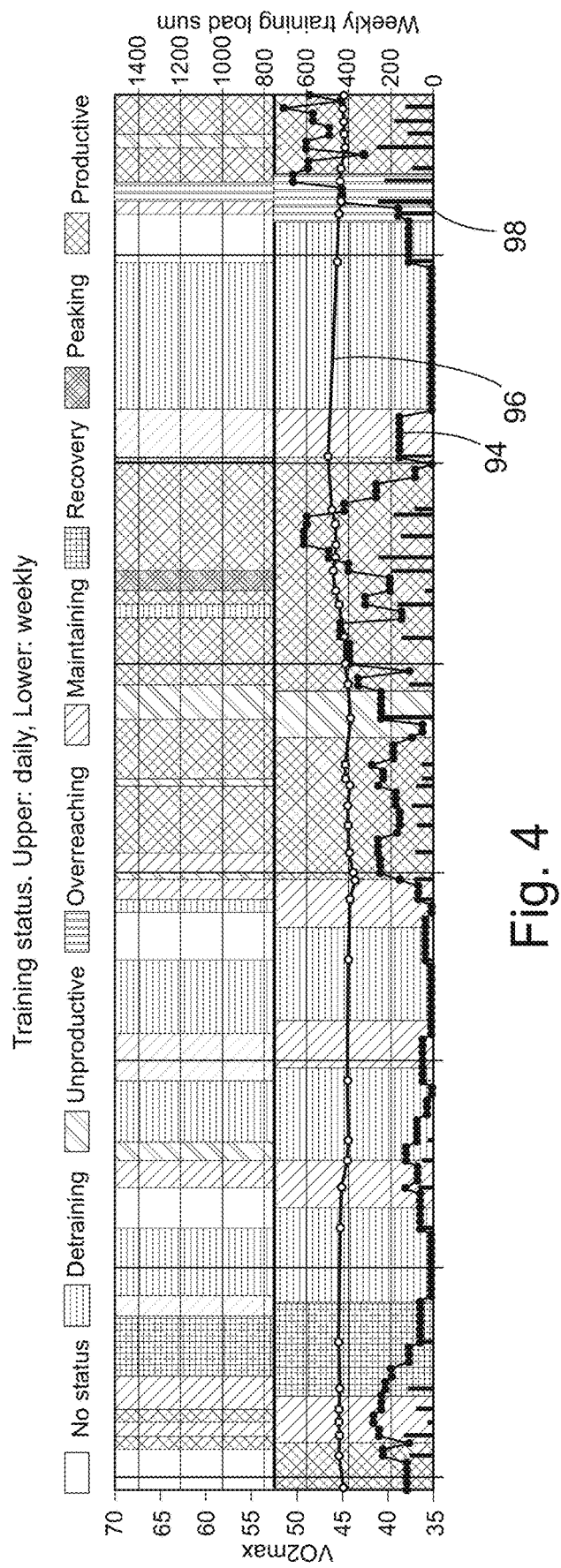
FIG. 4 represents calculation of advanced feedback in addition to basic feedback
Figure 6:
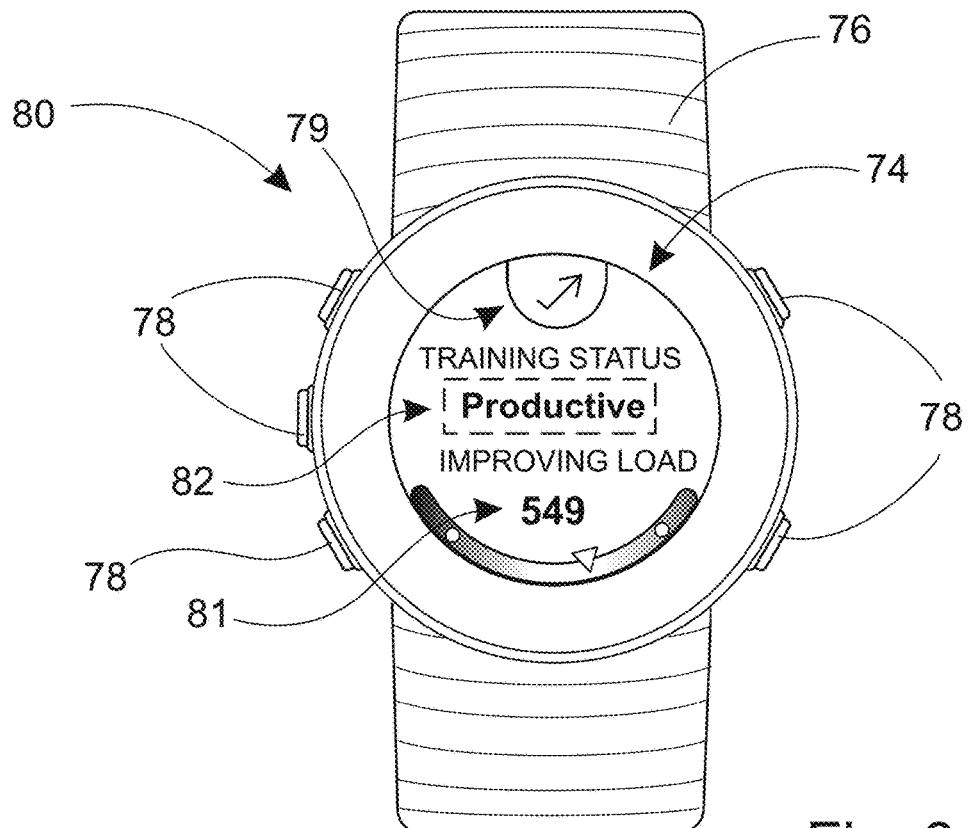
FIG. 6 represents another example to show training status to the user

FIG. 4 shows an example month-by-month training status chart, showing a total of 7 months of past training, with both a daily level portion and a weekly level portion. The various training statuses are illustrated by shading. The embodiment described above where the mode of the daily status is selected as a weekly status is illustrated in FIG. 6, wherein the most frequent daily training status of the week makes up the resultant weekly training status measurement. VO2Max line 96 in FIG. 4 represents the fluctuation of the user's fitness level over time, while training load sum line 94 represents the cumulative absolute training load of the previous 7 days. Optionally, training load peak 98 may additionally be displayed. Although the parameter VO2max is used, the chart would be similar when using recovery value instead.

Figure 5:
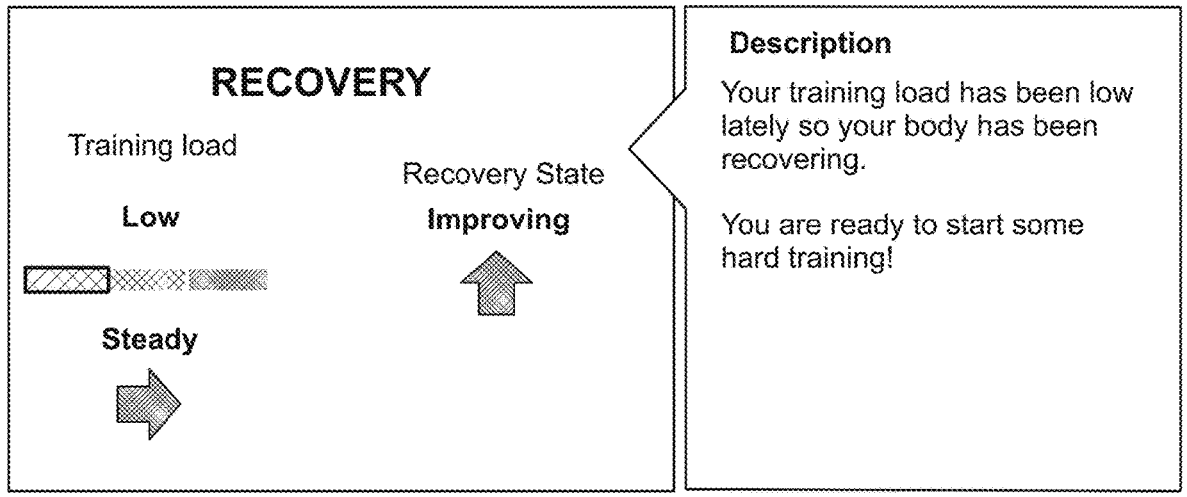
FIG. 5 represents an example of showing training status to the user

FIG. 5 is an illustrative example of how training status may be shown to a user, which may be displayed on an ordinary wrist top device having a host system for physiological measurements and analysis. The amount of information may vary based on the physical space available on the display, and may, for example, be displayed on multiple pages, or using graphical representations. In this example, "training load" is illustrated by a relative training load graphic as well as a training load trend graphic. Recovery state shows a text description and a trend graphic. All of this information is derived from calculation module 32 in FIG. 1A, and examples of possible text descriptions were shown in Table 2.

A further illustrative example of the presentation of the training status is shown in FIG. 6 showing a wrist top device 80 (worn on the wrist of a user held on the wrist by a strap 76) forming a user interface and used by a conventional fitness enthusiast or sportsperson. It has a display 74 with several fields. The result, the actual training status is shown literally in the field 82 and graphically in the field 79. Absolute weekly training load is shown in the field 81. The training status display may optionally have further screens that may be scrolled through to see further elaboration of the training status information, such as the information illustrated in FIG. 5.

Example Implementation:

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

Figure 7:
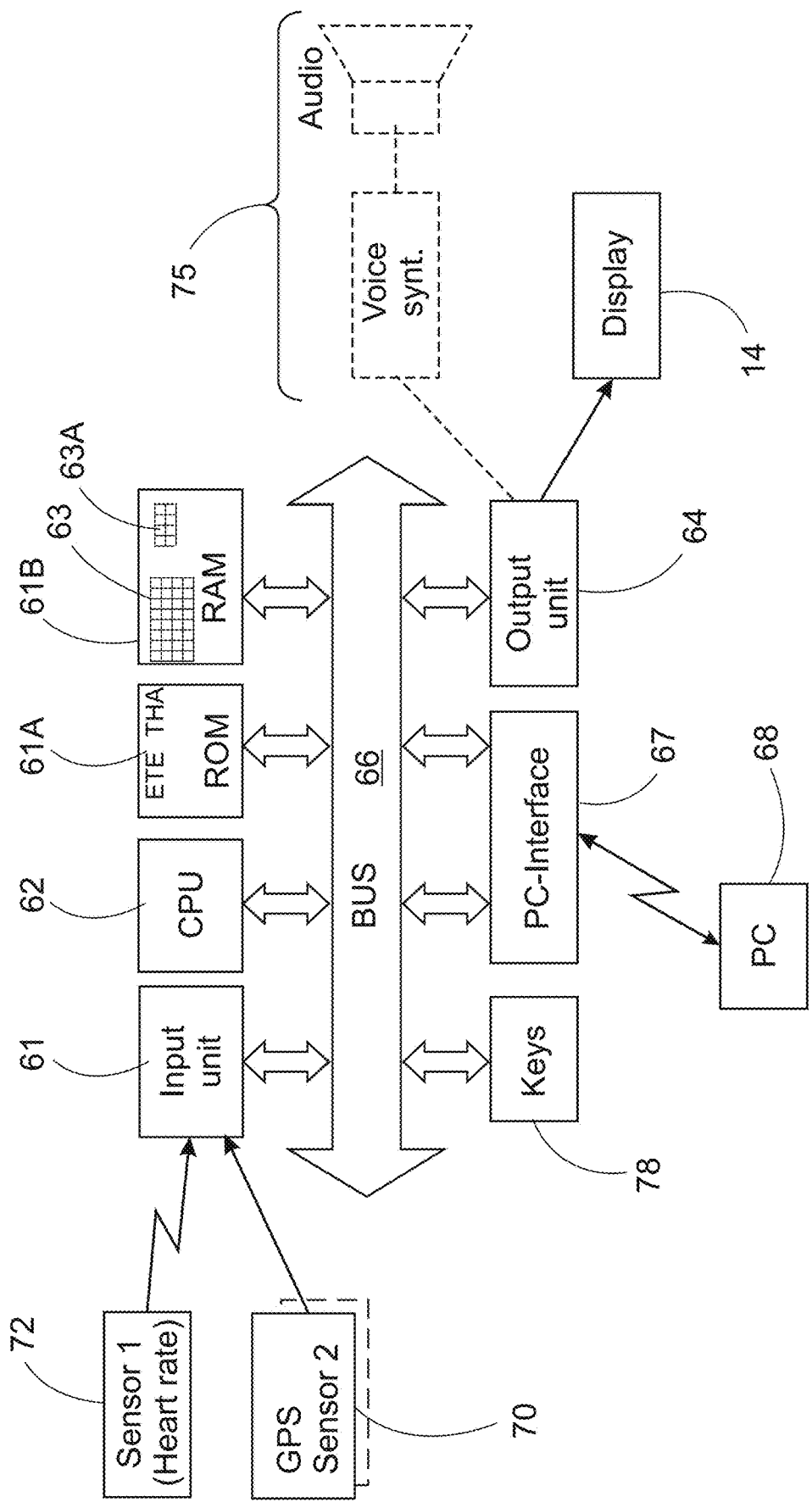
FIG. 7 represents an example of a hardware assembly The following table shows some exemplary definitions and abbreviations of terms used in the exemplary embodiments described herein.

According to exemplary FIG. 7, the implementation may include an assembly built around a central processing unit (CPU) 62. A bus 66 may transmit data between the central unit 62 and the other units. The input unit 61, ROM memory 61A RAM memory 61B including a dedicated memory 63A for the training status application and memory 63 for the host system, keys 78, PC connection 67, and output unit 64 may be connected to the bus.

The system may include a data logger which can be connected to cloud service, or other storage as would be understood by a person of ordinary skill in the art. The data logger may measure, for example, physiological response and/or external workload.

A heart rate sensor 72 and any sensor 70 registering external workload may be connected to the input unit 61, which may handle the sensor's data traffic to the bus 66. In some exemplary embodiments, the PC may be connected to a PC connection 67. The output device, for example a display 75 or the like, may be connected to output unit 64. In some embodiments, voice feedback may be created with the aid of, for example, a voice synthesizer and a loudspeaker 75, instead of, or in addition to the feedback on the display. The sensor 70 which may measure external workload may include any number of sensors, which may be used together to define the external work done by the user.

More specifically the apparatus presented in FIG. 7 may have the following parts for determining a training status:
- a heart rate sensor 72 configured to measure the heartbeat of the person, the heart rate signal being representative of the heartbeat of the user;
- optionally at least one sensor 70 to measure an external workload during an exercise, and
- a data processing unit 62 operably coupled to the said sensors 72, 70, a memory 61A, 61B operably coupled to the data processing unit 62,
- the memory may be configured to save background information of a user, for example, background data including an earlier performance level, user characteristics, and the like.

The apparatus may include dedicated software configured to execute the embodiments described in the present disclosure. The training status application requires RAM-memory 100-400 bytes (×8 bits), preferably 120-180 bytes. Each day requires 4 byte. Explained by way of example, 150 bytes covers 38 days, wherein the highest VO2max [16 bits], its exercise type [2 bits] and the sum of training load peaks [14] are recorded. Generally, calculation has a window of plurality of days, e.g. 7-60 days, preferably 30-50 days.

The invention claimed is:

1. A method for determining the training status of a user over a plurality of exercises using a portable device with a heart rate sensor, the device having a processor, a memory containing runtime and resident memory, and software, said determined training status derived from a combination of a measurement of a recovery state parameter and a fitness level parameter, the method comprising:
   retrieving, from the heart rate sensor, heart rate data from each of the plurality of exercises, and deriving, from the heart rate data, a fitness level parameter associated with each of the plurality of exercises;
   storing, in the memory, for each of the plurality of exercises, a set of chosen exercise characteristics including at least a date of the exercise and physical readiness level data for the exercise, the physical readiness level data comprising the fitness level parameter;
   retrieving, from the heart rate sensor, recovery heart rate data associated with one or more recovery periods, and deriving, from the recovery heart rate data, a recovery state parameter associated with each of the recovery periods;
   storing, in the memory, for each of the plurality of recovery periods, a set of chosen recovery characteristics, including at least a date of the recovery period and a recovery state parameter;
   calculating values of selection variables using the stored chosen exercise characteristics and chosen recovery characteristics in the resident memory, when the plurality of exercises and recovery state measurements have been executed, and storing calculated values into runtime memory; and
   determining the training status using sequential pre-determined selection rules, each rule being connected to one unique variable of said selection variables, wherein each selection rule uses a calculated value of its selection variable to limit a number of remaining alternatives and, after all selection rules have been sequentially used, only one alternative is selected.

2. The method according to claim 1, wherein the fitness level parameter is a VO2max value.

3. The method according to claim 1, wherein determining the training status further comprises:
   determining, based on the fitness level parameter, whether the user's fitness level has increased, and determining, based on the recovery state parameter, whether the user's recovery state parameter is at least a threshold value;
   when at least one of the following criteria is met: the user's fitness level has increased, and the user's recovery state parameter is at least the threshold value, generating and displaying a recommendation that the user can safely continue training.

4. The method according to claim 3, wherein the method further comprises:
   when at least one of the following criteria is met: the user's fitness level has decreased, and the user's recovery state parameter is not at least the threshold value, generating and displaying a recommendation that at least some elements of training should be changed.

5. The method according to claim 1, further comprising generating and displaying, from the stored chosen exercise characteristics and chosen recovery characteristics, a combined readiness index.

6. The method according to claim 1, further comprising providing, based on the stored chosen exercise characteristics and chosen recovery characteristics, a training status chart comprising a set of sequential training statuses, each of the sequential training statuses further associated with a determined training load peak.

7. A method for determining the training status of a user over a plurality of exercises using a portable device with a heart rate sensor, the device having a processor, a memory containing runtime and resident memory, and software, the method comprising:
   retrieving and analyzing, from the heart rate sensor, heart rate data from each of the plurality of exercises, wherein analyzing the heart rate data comprises determining, based on the data provided by the portable device, a type of exercise, and classifying the exercise as at least one of a first type or a second type;
   when the exercise is the first type, deriving, from the heart rate data, a fitness level parameter associated with each of the plurality of exercises, pairing the fitness level parameter with training load data, and storing, in the memory, for each of the plurality of exercises where the exercise is the first type, a first set of chosen exercise characteristics including at least a date of the exercise and physical readiness level data for the exercise, the physical readiness level data comprising the fitness level parameter and paired training load data;
   when the exercise is the second type, storing, in the memory, for each of the plurality of exercises where the exercise is the second type, a second set of chosen exercise characteristics including at least the date of the exercise and unpaired training load data, and combining the first set of chosen exercise characteristics and second set of chosen exercise characteristics in the memory as stored chosen exercise characteristics;
   retrieving, from the heart rate sensor, recovery heart rate data associated with one or more recovery periods, and deriving, from the recovery heart rate data, a recovery state parameter associated with each of the recovery periods;
   storing, in the memory, for each of the plurality of recovery periods, a set of chosen recovery characteristics, including at least a date of the recovery period and a recovery state parameter;

calculating values of selection variables using the stored chosen exercise characteristics and chosen recovery characteristics in the resident memory, when the plurality of exercises and recovery state measurements have been executed, and storing calculated values into runtime memory; and determining the training status using sequential pre-determined selection rules, each rule being connected to one unique variable of said selection variables, wherein each selection rule uses a calculated value of its selection variable to limit a number of remaining alternatives and, after all selection rules have been sequentially used, only one alternative is selected.

8. The method according to claim 7, wherein the fitness level parameter is a VO2max value.

9. The method according to claim 7, wherein the first type is at least one of: walking, running, or cycling.

10. The method according to claim 7, wherein at least one exercise is the first type, and determining the training status further comprises:
determining, based on the fitness level parameter, whether the user's fitness level has increased, and determining, based on the recovery state parameter, whether the user's recovery state parameter is at least a threshold value;
when at least one of the following criteria is met: the user's fitness level has increased, and the user's recovery state parameter is at least the threshold value, generating and displaying a recommendation that the user can safely continue training.

11. The method according to claim 10, wherein the method further comprises:
when at least one of the following criteria is met: the user's fitness level has decreased, and the user's recovery state parameter is not at least the threshold value, generating and displaying a recommendation that at least some elements of training should be changed.

12. The method according to claim 7, further comprising generating and displaying, from the stored chosen exercise characteristics and chosen recovery characteristics, a combined readiness index.

13. The apparatus according to claim 12, wherein the software is further arranged to perform a step of providing, based on the stored chosen exercise characteristics and chosen recovery characteristics, a training status chart comprising a set of sequential training statuses, each of the sequential training statuses further associated with a determined training load peak.

14. The method according to claim 7, further comprising providing, based on the stored chosen exercise characteristics and chosen recovery characteristics, a training status chart comprising a set of sequential training statuses, each of the sequential training statuses further associated with a determined training load peak.

15. An apparatus for determining a training status of a user from a plurality of exercises and recovery state measurements, comprising: a device with a heart rate sensor, the device having a processor, a memory including runtime and resident memory and software, said determined training status derived from a combination of a measurement of a recovery state parameter and a fitness level parameter, said software being arranged to perform the steps of:

retrieving, from the heart rate sensor, heart rate data from each of the plurality of exercises, and deriving, from the heart rate data, a fitness level parameter associated with each of the plurality of exercises;
storing, in the memory, for each of the plurality of exercises, a set of chosen exercise characteristics including at least a date of the exercise and physical readiness level data for the exercise, the physical readiness level data comprising the fitness level parameter;
retrieving, from the heart rate sensor, recovery heart rate data associated with one or more recovery periods, and deriving, from the recovery heart rate data, a recovery state parameter associated with each of the recovery periods;
storing, in the memory, for each of the plurality of recovery periods, a set of chosen recovery characteristics, including at least a date of the recovery period and a recovery state parameter;
calculating values of selection variables using the stored chosen exercise characteristics and chosen recovery characteristics in the resident memory, when the plurality of exercises and recovery state measurements have been executed, and storing calculated values into runtime memory; and
determining the training status using sequential pre-determined selection rules, each rule being connected to one unique variable of said selection variables, wherein each selection rule uses a calculated value of its selection variable to limit a number of remaining alternatives and, after all selection rules have been sequentially used, only one alternative is selected.

16. The apparatus according to claim 15, wherein the fitness level parameter is a VO2max value.

17. The apparatus according to claim 15, wherein determining the training status further comprises:
determining, based on the fitness level parameter, whether the user's fitness level has increased, and determining, based on the recovery state parameter, whether the user's recovery state parameter is at least a threshold value;
when at least one of the following criteria is met: the user's fitness level has increased, and the user's recovery state parameter is at least the threshold value, generating and displaying a recommendation that the user can safely continue training.

18. The apparatus according to claim 17, wherein the software is further arranged to perform a step of:
when at least one of the following criteria is met: the user's fitness level has decreased, and the user's recovery state parameter is not at least the threshold value, generating and displaying a recommendation that at least some elements of training should be changed.

19. The apparatus according to claim 15, wherein the software is further arranged to perform a step of generating and displaying, from the stored chosen exercise characteristics and chosen recovery characteristics, a combined readiness index.

20. The apparatus according to claim 15, wherein an output device is implemented in at least one of the following: a heart rate monitor, a fitness device, a mobile phone, a PDA device, a wrist top computer, a tablet computer or a personal computer.

* * * * *